(12) United States Patent
Yang et al.

(10) Patent No.: US 6,382,254 B1
(45) Date of Patent: May 7, 2002

(54) MICROFLUIDIC VALVE AND METHOD FOR CONTROLLING THE FLOW OF A LIQUID

(75) Inventors: Zhihao Yang, Webster; Ravi Sharma, Fairport, both of NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/735,322

(22) Filed: Dec. 12, 2000

(51) Int. Cl.⁷ .............................. F15B 21/00; F15C 1/04; F16K 49/00; F16K 31/00
(52) U.S. Cl. ...................... 137/807; 137/341; 137/828; 251/11
(58) Field of Search ........................... 251/11; 137/807, 137/828, 341, 13

(56) References Cited

U.S. PATENT DOCUMENTS

| | | | | |
|---|---|---|---|---|
| 3,563,258 A | * | 2/1971 | Hechler, IV | 137/1 |
| 3,592,207 A | * | 7/1971 | Borello | 137/1 |
| 3,787,187 A | * | 1/1974 | De Witt | 137/2 |
| 4,049,491 A | * | 9/1977 | Brandon et al. | 137/4 |
| 4,546,784 A | * | 10/1985 | Schulz et al. | 137/13 |
| 4,921,902 A | * | 5/1990 | Evani et al. | 137/13 |
| 5,171,132 A | | 12/1992 | Miyazaki et al. | |
| 5,272,724 A | | 12/1993 | Solomon et al. | |
| 6,068,751 A | | 5/2000 | Neukermans | |
| 6,160,036 A | * | 12/2000 | Kommareddi et al. | 137/13 |

FOREIGN PATENT DOCUMENTS

| | | |
|---|---|---|
| EP | 0 568 902 | 11/1993 |
| GB | 2 248 891 | 4/1992 |

* cited by examiner

*Primary Examiner*—Philippe Derakshani
*Assistant Examiner*—D. Austin Bonderer
(74) *Attorney, Agent, or Firm*—Harold E. Cole

(57) ABSTRACT

A microfluidic valve for controlling the flow of a material through a microfluidic channel comprising:
  a) a microfluidic channel comprising a passageway,
  b) a heater in contact with at least a portion of the microfluidic channel,
  c) a carrier fluid comprising the material and an amount of thermally-responsive material so that the carrier fluid can be thickened by heat from the heater to cause a reduction in flow of the carrier fluid through the microfluidic channel.

18 Claims, 1 Drawing Sheet

MICROFLUIDIC VALVE AND METHOD FOR CONTROLLING THE FLOW OF A LIQUID

FIELD OF THE INVENTION

This invention relates to a microfluidic valve and method for regulating the flow of minute quantities of liquid.

BACKGROUND OF THE INVENTION

Microfluidic systems are very important in several applications. For example, U.S. Pat. No. 5,445,008 discloses these systems in biomedical research such as DNA or peptide sequencing. U.S. Pat. No. 4,237,224 discloses such systems used in clinical diagnostics such as blood or plasma analysis. U.S. Pat. No. 5,252,743 discloses such systems used in combinatorial chemical synthesis for drug discovery. U.S. Pat. No. 6,055,002 also discloses such systems for use in ink jet printing technology.

Valves and pumps are the two most fundamental components in controlling the fluid dynamics in a microfluidic system. Various efforts have been made to build miniature valves and pumps for microfluidic systems by micro-machining silicon. Several valves and pumps have been disclosed using mechanical actuators, such as piezoelectric actuators or spring-loaded magnetic actuators. Examples of these are disclosed in U.S. Pat. Nos. 6,068,751; 5,171,132; 5,272,724; UK Patent 2,248,891, and European Patent 568,902. However, there are problems with these mechanically actuated microfluidic devices since they are complex in design, difficult to fabricate and suffer from a lack of mechanical durability and reliability. In addition, these valves are prone to leak because there are problems in producing a good seal. These problems generally result in the high cost, low productivity, and inoperability of these microfluidic devices.

The compatibility in fabrication of the microfluidic devices with the procedure of semiconductor chip manufacturing industry is another important issue in achieving low cost microfluidic systems with mass production. In addition, for those more sophisticated microfluidic systems, a complex micro-valves and pumps system is often necessary to regulate the liquid in the devices. Therefore, an on-chip integrated circuit to control the individual valves and pumps is highly desired. This also requires the microfluidic devices to be compatible with IC fabrication such as the Complementary Metal Oxide System (CMOS) fabrication in the semiconductor industry.

It is an object of this invention to provide to provide a microfluidic valve for controlling the flow of a material through a microfluidic channel and a method for controlling the flow of a material through a microfluidic channel without any mechanical actuation or moving parts.

It is another object of this invention to provide a microfluidic valve using an integrated heater in combined with a specially formulated thermal responsive solution to control the fluid passing through a micro-fluidic channel avoiding any mechanical actuation.

It is another object of this invention to provide a microfluidic valve that can be readily fabricated using standard CMOS fabrication technology in the semiconductor industry.

SUMMARY OF THE INVENTION

These and other objects are achieved in accordance with this invention comprising a microfluidic valve for controlling the flow of a material through a microfluidic channel comprising:
a) a microfluidic channel comprising a passageway,
b) a heater in contact with at least a portion of the microfluidic channel, c) a carrier fluid comprising the material and an amount of thermally-responsive material so that the carrier fluid can be thickened by heat from the heater to cause a reduction in flow of the carrier fluid through the microfluidic channel.

Another embodiment of the invention relates to method for controlling the flow of a material through a microfluidic channel comprising heating a carrier fluid in a microfluidic channel, the carrier fluid comprising the material and an amount of thermally-responsive material, the heating causing the carrier fluid to be thickened by heat to cause a reduction in flow of the carrier fluid through the microfluidic channel.

By use of the invention, a low cost microfluidic valve can be obtained. In addition, the invention can be used with an on-chip integrated circuit to control individual valves.

DETAILED DESCRIPTION OF THE PREFERRED EMBODIMENTS

Figure 1:
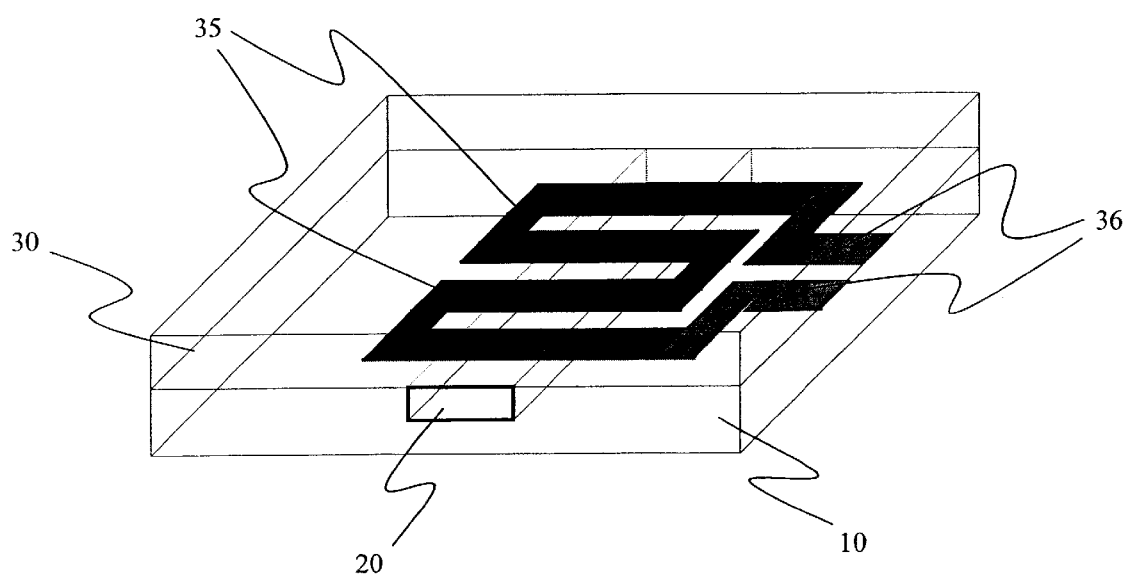
FIG. 1 illustrates a microfluidic valve with an upper layer 30 and a lower layer 10. Heater 35 having electrical interconnects 36 is in contact with the top wall of microfluidic channel 20. The electrical interconnects may be a conducting material, such as aluminum or copper, to serve as wires to connect the heaters to an external power supply.

The term, "microfluidic", "microscale" or "microfabricated" generally refers to structural elements or features of a device, such as fluid channels, chambers or conduits, having at least one fabricated dimension in the range from about 0.1 $\mu$m to about 500 $\mu$m. In the devices of present invention, the microscale channels or chambers preferably have at least one internal cross-section dimension, e.g., depth, width, length, diameter, etc., between about 0.1 $\mu$m to about 200 $\mu$m, preferably between about 1 $\mu$m to about 100 $\mu$m.

The microfluidic devices described in present invention are preferably fabricated with the techniques commonly associated with the semiconductor electronics industry, e.g., photolithography, dry plasma etching, wet chemical etching, etc., on the surface of a suitable substrate material, such as silicon, glass, quartz, ceramics, as well as polymeric substrates, e.g., plastics. In a preferred embodiment of the invention, microfluidic devices typically comprise two or more layers of fabricated components that are appropriately mated or joined together.

Various techniques using chip technology for the fabrication of microfluidic devices, and particularly microcapillary devices, with silicon and glass substrates have been discussed by Manz, et al. (*Trends in Anal. Chem.* 1990, 10, 144, and *Adv. In Chromatog.* 1993, 33, 1). Other techniques such as laser ablation, air abrasion, injection molding, embossing, etc., are also known to be used to fabricate microfluidic devices, assuming compatibility with the selected substrate materials.

The function of a microfluidic valve is to control the flow rate or volume flux of a liquid through a micro-capillary channel. In general, for a fluid with a viscosity of $\mu$ driven through a micro-capillary channel with a length of L by a pressure of P, the volume flux, Q, of the liquid pass through the channel is:

$$Q = \frac{P}{\mu L} \cdot f,$$

where f is the dimension factor of the cross-section for the microfluidic channel. For a circular cross-section capillary channel with a radio of r:

$$f_c = \frac{\pi r^4}{8},$$

while for a rectangular cross-section channel with a width of a and height of b with the aspect ratio of θ=b/a (η≧1), $$f_R = a^4 \left[ \frac{\eta}{12} - \frac{16}{\pi^5} \tanh\left(\frac{\pi}{2}\eta\right) \right].$$

It is generally true that the flow rate or the volume flex is inversely proportional to the internal viscosity of fluid in the channel. Therefore, if one can control the viscosity of the fluid in the channel, one can indeed control the flow rate of the fluid passing though the channel.

In a preferred embodiment of the invention, a microfluidic valve is designed utilizing the property of a specially formulated fluid serving as the carrier fluid for transport of subject materials through the microfluidic channels for various of purpose.

The "subject materials" simply refers to the materials, such as chemical or biological compounds, of interest, which may also include a variety of different compounds, including chemical compounds, mixtures of chemical compounds, e.g., a dye, a pigment, a protein, DNA, a peptide, an antibody, an antigen, a cell, an organic compound, a surfactant, an emulsion, a dispersion, a polysaccharide, colloidal particles, organic or inorganic compounds, nucleic acids, or extracts made from biological materials, such as bacteria, plains, fungi, or animal cells or tissues, naturally occurring or synthetic compositions. The viscosity of the formulated fluid is sensitive to the temperature, and preferably increases with the increase of temperature.

In another preferred embodiment of the invention, the thermally-responsive material comprises at least one kind of block copolymer with at least one block comprising poly (ethylene oxide), or PEO. In another preferred embodiment of the invention, the thermally-responsive material comprises a tri-block copolymer of poly(ethylene oxide)-poly (propylene oxide)-poly(ethylene oxide), or PEO-PPO-PEO dissolved in an aqueous solution. The preferred concentrations of the solutions are from about 5% to about 80%, preferably from 10% to 40% in weight.

The solutions at room temperature, e.g., 22° C., are fluidic with a typical viscosity less than 10 centipoise (cP). The viscosity of the formulated solutions increases dramatically when raising the temperature from about 30° C. to about 80° C., as the solutions rapidly form non-fluidic gels at the elevated temperature. The viscosity change of the formulated solutions in response of temperature change is entirely reversible as the solutions turn to fluidic having the original viscosity when cooled down to its initial temperature.

In another preferred embodiment, a methyl cellulose polymer may be used as a thermally-responsive material in the carrier fluid. For example, 2.75 wt. % solution of METHOCEL® K100LV (Dow Chemical Co.) having a viscosity of about 1 poise at 50° C. and a viscosity of more than 10 poise at 75° C. can be used.

FIG. 1 illustrates an example of the microfluidic valve of the invention. This device comprises an upper layer 30 and a lower layer 10. A microfluidic channel 20 is fabricated on the upper surface of the lower layer substrate material, which may be silicon, glass, quartz, ceramics, as well as polymeric substrates, e.g., plastics, such as polyamide, polymethylmethacrylate (PMMA), polycarbonate, polytetrafluoroethylene, Teflon®, polydimethylsiloxane (PDMS), polyvinylchloride (PVC), polysulfone, etc. Such polymeric substrates can be fabricated either by the microfabrication techniques described above, or by molding from microfabricated masters, such as injection mold, embossing or polymerizing the precursor material within the mold (see U.S. Pat. No. 5,512,131). In addition, it is known in the art that microfluidic channels may be fabricated using photoresist material such as SU-8® (MicroChem Corp.).

A heater 35, preferably made from appropriately doped polysilicon, is fabricated on the lower surface of the upper layer substrate, which may also be silicon, glass, quartz, ceramics, or polymeric materials. A conducting material 36, such as aluminum or copper, is also integrated to serve as wires to connect the heater to an external power supply. In a preferred embodiment of the invention, the microfluidic devices are fabricated using CMOS compatible fabrication techniques, and the heaters are integrated with a CMOS circuit on the chip, which controls the signals or voltages applied to the heaters to activate the valve.

In another embodiment of the invention, heaters may be located on both upper and lower substrates 50 of the microfluidic channel 40. This will increase the heat transport efficiency and increase the thermal activation speed of the valve. In still another embodiment of the invention, increased thermal activation speed may be achieved using a "fin" heater which consists of a group of parallel heater elements in the microfluidic channel.

The following example illustrates the utility of the present invention.

EXAMPLE

Viscosity vs. Temperature of Thermally-responsive Solutions

Thermally-responsive solutions were formulated by dissolving a tri-block copolymer of poly(ethylene oxide)-poly (propylene oxide)-poly(ethylene oxide), or PEO-PPO-PEO in an aqueous solution. A series of the PEO-PPO-PEO tri-block copolymers were obtained from BASF under the product trade name of Pluronic®.

A Rheometrics ARES Fluids Spectrometer, from Rheometric Scientific, Inc., equipped with a corvette geometry, was used to measure the oscillatory shear properties of the Pluronic® solutions. Dynamic viscosity was measured continuously as the temperature was ramped from 20° C. to 80° C. The typical ramp rate was 1° C./minute. The fluids were initially characterized at 20° C. a continuous shear experiment covering a typical range of shear rates from 1 to 100/second. All were found to have low viscosity and Newtonian response. For the temperature scan experiments, a monitoring frequency of 10 radians/-second was used.

The results are shown in the following tables:

TABLE 1

| Temperature | Viscosity (Poise) of Pluronic ® P85 Solutions | | |
|---|---|---|---|
| (° C.) | 20% | 15% | 10% |
| 25 | 0.09 | 0.037 | 0.022 |
| 30 | 0.112 | 0.033 | 0.017 |
| 35 | 0.113 | 0.031 | 0.014 |
| 40 | 0.096 | 0.026 | 0.012 |
| 45 | 0.079 | 0.022 | 0.01 |
| 50 | 0.066 | 0.019 | 0.008 |
| 55 | 0.054 | 0.016 | 0.007 |
| 60 | 0.05 | 0.014 | 0.006 |
| 62 | 0.069 | 0.016 | 0.007 |
| 64 | 0.143 | 0.029 | 0.011 |

TABLE 1-continued

| Temperature | Viscosity (Poise) of Pluronic® P85 Solutions | | |
|---|---|---|---|
| (° C.) | 20% | 15% | 10% |
| 66 | 0.382 | 0.065 | 0.022 |
| 68 | 1.283 | 0.185 | 0.059 |
| 70 | 5.176 | 0.792 | 0.194 |
| 72 | 15.018 | 3.684 | 0.821 |
| 74 | 31.802 | 11.303 | 3.534 |
| 76 | 46.005 | 21.505 | 9.134 |
| 78 | 52.008 | 28.574 | 13.39 |
| 80 | 51.921 | 30.369 | 17.917 |

TABLE 2

Viscosity of 25% Pluronic® L62 Solution

| Temperature (° C.) | Viscosity (Poise) |
|---|---|
| 22 | 0.072 |
| 25 | 0.068 |
| 28 | 0.069 |
| 30 | 0.073 |
| 32 | 0.081 |
| 34 | 0.1 |
| 36 | 0.136 |
| 38 | 0.237 |
| 40 | 0.44 |
| 42 | 0.834 |
| 44 | 0.976 |
| 46 | 1.777 |
| 48 | 5.864 |
| 49 | 26.704 |
| 50 | 37.107 |
| 52 | 40.677 |
| 54 | 35.045 |
| 56 | 31.245 |

TABLE 3

Viscosity of 22% Pluronic® F87 Solution

| Temperature (° C.) | Viscosity (Poise) |
|---|---|
| 22 | 0.201 |
| 25 | 0.242 |
| 30 | 0.525 |
| 32 | 0.696 |
| 34 | 0.968 |
| 36 | 1.225 |
| 37 | 1.505 |
| 38 | 385 |
| 39 | 13873 |
| 40 | 17046 |
| 41 | 15056 |
| 42 | 14963 |
| 45 | 14512 |
| 50 | 15008 |
| 55 | 15509 |

The above results show that the Pluronic® P85 solutions with the concentrations from 10% to 20% have viscosity increases of more than 3 orders of magnitude when the temperature increases from 60° C. to 80° C., the 25% Pluronic® L62 solution has a orders of magnitude viscosity increase with temperature from 30° C. to 50° C. 22% Pluronic® F87 solution has a more than 5 orders of magnitude viscosity increase with temperature from 30° C. to 40° C. The results demonstrated that these fluids are thermally-responsive and can be used in the device and method of the invention.

The invention has been described in detail with particular reference to certain preferred embodiments thereof, but it will be understood that variations and modifications can be effected within the spirit and scope of the invention.

What is claimed is:

1. A microfluidic valve for controlling the flow of a subject material through a microfluidic channel comprising:
   a) a microfluidic channel comprising a passageway,
   b) a heater in contact with at least a portion of said microfluidic channel,
   c) a carrier fluid comprising said subject material and an amount of thermally-responsive material so that said carrier fluid can be thickened by heat from said heater to cause a reduction in flow of said carrier fluid through said microfluidic channel.

2. The valve of claim 1 wherein said thermally-responsive material can be gelled by heat from said heater.

3. The valve of claim 1 wherein said thermally-responsive material is a polyethylene oxide-containing block copolymer.

4. The valve of claim 3 wherein said polyethylene oxide-containing block copolymer is a tri-block copolymer of polyethylene oxide-polypropylene oxide-polyethylene oxide.

5. The valve of claim 1 wherein said thermally-responsive material is a methyl cellulose polymer.

6. The valve of claim 1 wherein said carrier fluid comprises from about 0.01 to about 70% by weight of thermally-responsive material.

7. The valve of claim 1 wherein said subject material comprises a dye, a pigment, a protein, DNA, a peptide, an antibody, an antigen, a cell, an organic compound, a surfactant, an emulsion, a dispersion, a polysaccharide, colloidal particles, organic or inorganic compounds, nucleic acids, or extracts made from biological materials.

8. The valve of claim 1 wherein said heater is contained in said microfluidic channel.

9. The valve of claim 1 wherein said passageway is enclosed by silicon, glass, polyimide, quartz, ceramic, polymethylmethacrylate, polydimethylsiloxane or photoresist material.

10. The valve of claim 1 wherein said passageway is partially enclosed.

11. The valve of claim 10 wherein said passageway is a groove.

12. A method for controlling the flow of a material through a microfluidic channel comprising heating a carrier fluid in a microfluidic channel, said carrier fluid comprising said subject material and an amount of thermally-responsive material, said heating causing said carrier fluid to be thickened by heat to cause a reduction in flow of said carrier fluid through said microfluidic channel.

13. The method of claim 12 wherein said thermally-responsive material can be gelled by heat.

14. The method of claim 12 wherein said thermally-responsive material is a polyethylene oxide-containing block copolymer.

15. The method of claim 14 wherein said polyethylene oxide-containing block copolymer is a tri-block copolymer of polyethylene oxide-polypropylene oxide-polyethylene oxide.

16. The method of claim 12 wherein said thermally-responsive material is a methyl cellulose polymer.

17. The method of claim 12 wherein said carrier fluid comprises from about 0.01 to about 70% by weight of thermally-responsive material.

18. The method of claim 12 wherein said subject material comprises a dye, a pigment, a protein, DNA, a peptide, an antibody, an antigen, a cell, an organic compound, a surfactant, an emulsion, a dispersion, a polysaccharide, colloidal particles, organic or inorganic compounds, nucleic acids, or extracts made from biological materials.

* * * * *